US008170679B2

(12) United States Patent
Saoji et al.

(10) Patent No.: US 8,170,679 B2
(45) Date of Patent: *May 1, 2012

(54) SPECTRAL CONTRAST ENHANCEMENT IN A COCHLEAR IMPLANT SPEECH PROCESSOR

(75) Inventors: Aniket Saoji, Northridge, CA (US); Leonid M. Litvak, Los Angeles, CA (US); Gene Y. Fridman, Santa Clarita, CA (US)

(73) Assignee: Advanced Bionics, LLC, Valencia, CA (US)

( * ) Notice: Subject to any disclaimer, the term of this patent is extended or adjusted under 35 U.S.C. 154(b) by 30 days.

This patent is subject to a terminal disclaimer.

(21) Appl. No.: 12/765,649

(22) Filed: Apr. 22, 2010

(65) Prior Publication Data

US 2010/0234920 A1 Sep. 16, 2010

Related U.S. Application Data

(63) Continuation of application No. 11/386,198, filed on Mar. 21, 2006, now Pat. No. 7,729,775.

(51) Int. Cl.
*A61N 1/00* (2006.01)

(52) U.S. Cl. ........................................ 607/57

(58) Field of Classification Search .............. 607/24–28, 607/136, 137, 55–57; 600/27–28, 559; 73/585; 181/126–130; 381/23.1, 312–331; 623/24; 128/899

See application file for complete search history.

(56) References Cited

U.S. PATENT DOCUMENTS

| | | | |
|---|---|---|---|
| 3,894,195 A * | 7/1975 | Kryter | 381/23.1 |
| 4,532,930 A | 8/1985 | Crosby et al. | |
| 4,793,353 A | 12/1988 | Borkan | |
| 4,819,647 A | 4/1989 | Byers et al. | |
| 5,626,629 A | 5/1997 | Faltys et al. | |
| 5,749,912 A | 5/1998 | Zhang et al. | |
| 5,868,682 A * | 2/1999 | Combs et al. | 600/559 |
| 5,991,663 A | 11/1999 | Irlicht et al. | |
| 6,129,753 A | 10/2000 | Kuzma | |
| 6,154,678 A | 11/2000 | Lauro | |

(Continued)

FOREIGN PATENT DOCUMENTS

WO 2004/043537 5/2004

OTHER PUBLICATIONS

U.S. Appl. No. 11/008,869, filed Dec. 9, 2004, Segel.

(Continued)

*Primary Examiner* — Eric D. Bertram
*Assistant Examiner* — Elizabeth K So
(74) *Attorney, Agent, or Firm* — Wong, Cabello, Lutsch, Rutherford & Brucculeri, L.L.P.

(57) ABSTRACT

Psychophysical tests are administered to cochlear implant (CI) users to determine a spectral modulation transfer function (SMTF), smallest detectable spectral contrast as a function of spectral modulation frequency, for each individual CI user. The determined SMTF for individual CI user is compared against a SMTF of a normal hearing person to determine the specific enhancements needed. A profile of spectral enhancement achievable with variation of filter parameters, sigma and maximum that best fits the needed enhancements for the individual CI user is selected. Based on the corresponding sigma and maximum selected, a sound processing strategy is adjusted to provide customized spectral contrast enhancement for the individual CI user. The sound processing strategy implemented includes an outer hair cell model.

22 Claims, 8 Drawing Sheets

U.S. PATENT DOCUMENTS

| | | | |
|---|---|---|---|
| 6,157,861 A | 12/2000 | Faltys et al. | |
| 6,216,045 B1 | 4/2001 | Black et al. | |
| 6,219,580 B1 | 4/2001 | Faltys et al. | |
| 6,289,247 B1 | 9/2001 | Faltys et al. | |
| 6,308,101 B1 | 10/2001 | Faltys et al. | |
| 6,600,955 B1 | 7/2003 | Zierhofer | |
| 6,728,578 B1 | 4/2004 | Voelkel | |
| 6,745,155 B1 | 6/2004 | Andringa et al. | |
| 6,775,389 B2 | 8/2004 | Harrison et al. | |
| 6,778,858 B1 | 8/2004 | Peeters | |
| 6,826,430 B2 | 11/2004 | Faltys et al. | |
| 6,873,709 B2 * | 3/2005 | Hou | 381/106 |
| 6,970,570 B2 | 11/2005 | Goldstein | |
| 6,980,864 B2 | 12/2005 | Faltys et al. | |
| 7,003,876 B2 | 2/2006 | Crawford et al. | |
| 7,082,332 B2 | 7/2006 | Blamey et al. | |
| 7,171,272 B2 | 1/2007 | Blamey et al. | |
| 7,200,504 B1 | 4/2007 | Fister | |
| 7,203,548 B2 | 4/2007 | Whitehurst et al. | |
| 7,225,027 B2 | 5/2007 | Zeng et al. | |
| 7,242,985 B1 | 7/2007 | Fridman et al. | |
| 7,277,760 B1 | 10/2007 | Litvak et al. | |
| 7,292,890 B2 | 11/2007 | Whitehurst et al. | |
| 7,292,891 B2 | 11/2007 | Hartley et al. | |
| 7,292,892 B2 | 11/2007 | Litvak et al. | |
| 7,308,303 B2 | 12/2007 | Whitehurst et al. | |
| 7,310,558 B2 | 12/2007 | Van Hoesel | |
| 7,317,945 B2 | 1/2008 | Litvak et al. | |
| 7,349,741 B2 | 3/2008 | Maltan et al. | |
| 7,450,994 B1 | 11/2008 | Mishra et al. | |
| 7,496,405 B1 * | 2/2009 | Litvak et al. | 607/56 |
| 7,522,961 B2 | 4/2009 | Fridman et al. | |
| 2004/0015204 A1 | 1/2004 | Whitehurst et al. | |
| 2004/0015205 A1 | 1/2004 | Whitehurst et al. | |
| 2004/0082980 A1 | 4/2004 | Mouine et al. | |
| 2004/0230254 A1 | 11/2004 | Harrison et al. | |
| 2005/0137651 A1 | 6/2005 | Litvak et al. | |
| 2005/0234366 A1 * | 10/2005 | Heinz et al. | 600/559 |
| 2006/0100672 A1 | 5/2006 | Litvak | |
| 2006/0229688 A1 | 10/2006 | McClure et al. | |
| 2007/0021800 A1 | 1/2007 | Whitehurst et al. | |
| 2007/0055308 A1 | 3/2007 | Haller et al. | |
| 2007/0123938 A1 | 5/2007 | Haller et al. | |
| 2007/0260292 A1 | 11/2007 | Faltys et al. | |

OTHER PUBLICATIONS

U.S. Appl. No. 11/089,171, filed Mar. 24, 2005, Hahn.
U.S. Appl. No. 11/122,648, filed May 5, 2005, Griffith.
U.S. Appl. No. 11/178,054, filed Jul. 8, 2005, Faltys.
U.S. Appl. No. 11/226,777, filed Sep. 13, 2005, Faltys.
U.S. Appl. No. 11/261,432, filed Oct. 28, 2005, Mann.
U.S. Appl. No. 11/262,055, filed Dec. 28, 2005, Fridman.
U.S. Appl. No. 11/387,206, filed Mar. 23, 2006, Harrison.
Carney, L.H., "A model for the responses of low-frequency auditory-nerve fibers in cat", J. Acoust Soc. Am. 93(1):401-417 (1993).
Deutsch et al., "Understanding the Nervous system, an Engineering Perspective", IEEE Press, Chap. 9, pp. 181-225 (1993).
Geurts, L. and J. Wouters, "Enhancing the speech envelope of continuous interleaved sampling processors for cochlear implants", J. Acoust Soc. Am. 105(4):2476-84 (1999).
Moore, Brian C.J., "An Introduction to the Psychology of Hearing", $4^{th}$ Edition, Academic Press, pp. 9-12 (1997).
Srulovicz et al., "A Central Spectrum Model: A Synthesis of Auditory-Nerve Timing and Place Cues in Monaural Communication of Frequency Spectrum", J. Acoust. Soc. Am., vol. 73, pp. 1266-1276 (1983).

* cited by examiner

710 — FIT A SHAPE FUNCTION $H(cpo,\sigma)$ TO SMTF OF CI USER

712 — FIT A ENHANCEMENT FUNCTION $F(cpo,\sigma, G_{max}, G_{min})$ TO SMTF OF CI USER 714 — DETERMINE $\sigma$, $G_{max}$, AND $G_{min}$ THAT BEST MATCHES THE SMTF OF CI USER 716 — APPLY DETERMINED $\sigma$, $G_{max}$, AND $G_{min}$ TO ADJUST A SOUND PROCESSING STRATEGY SPECIFICALLY TAILORED TO THE CI USER

SPECTRAL CONTRAST ENHANCEMENT IN A COCHLEAR IMPLANT SPEECH PROCESSOR

RELATED APPLICATIONS

This application is a continuation of U.S. patent application Ser. No. 11/386,198 (now U.S. Pat. No. 7,729,775), filed Mar. 21, 2006 and entitled "Spectral Contrast Enhancement in a Cochlear Implant Speech Processor," which is hereby incorporated by reference.

TECHNICAL FIELD

The following disclosure relates to implantable neurostimulator devices and systems, for example, cochlear stimulation systems, and to sound processing strategies employed in conjunction with such systems.

BACKGROUND

Prior to the past several decades, scientists generally believed that it was impossible to restore hearing to the profoundly deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech. The electrical stimulation is implemented through a prosthetic device, known as a cochlear implant (CI), which is implanted in the inner ear.

Cochlear implants generally employ an electrode array that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. These are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

A sound coding strategy is an algorithm that translates signals picked up by a microphone into a sequence of electric pulses that can be transmitted to the intra-cochlear electrodes. While existing sound coding strategies can support satisfactory recognition of speech in quiet environments, subjects' speech comprehension can decrease dramatically in difficult listening conditions. Some causes of poor performance in demanding listening tasks may be partially attributed to sound processing strategies themselves. For example, all strategies assume that each channel is represented independently in the cochlea. However, the performance of CI users can generally be worse than that of normal-hearing subjects listening through cochlear implant simulators with a similar number of channels. This suggests that a substantial amount of channel interaction can occur in cochlear implant subjects. Channel interaction may "smear" spectral peaks that are essential, for example, for encoding vowel identity. Thus, performance of some CI subjects might be improved by utilizing a strategy that emphasizes peaks in short-term spectra.

Accordingly, a U.S. patent application Ser. No. 11/003,155 (now U.S. Pat. No. 7,242,985), incorporated herein in its entirety by reference, discloses a cochlear stimulation system that accounts for the interaction between frequency bands and thereby enhances the contrast between neighboring signals. The cochlear stimulation system implements an outer hair cell model strategy in which lateral suppression coefficients are adjusted to distinguish the contributions of individual signals to the composite signal defining a sound. In general, this is accomplished by dividing an audio signal into multiple input signals such that each input signal is associated with a particular frequency band. Each of the input signals can then be scaled in accordance with respective scaling factors representing the separation between different frequency bands. Once scaled, the multiple input signals can be converted into simulation signals that represent the laterally suppressed sound.

Another contrast enhancement strategy, the Moving Picture Experts Group MP3 audio layer 3 (MP3) strategy, is based on a psychoacoustic model which recognizes that there are certain sounds that a human ear cannot hear. Psychoacoustics describes a relationship between physics of sounds and their perception. An absolute hearing threshold and masking are two fundamental phenomena in psychoacoustics. The absolute hearing threshold is the minimum intensity for the human ear to detect sound at a given frequency in quiet. Masking describes the nonlinearly raised threshold for the human ear to detect sound in the presence of an existing masking signal. The human ear has a naturally masking function. If two sounds are very different but one is much louder than the other, the human ear may not perceive the quieter signal. While hearing capacity varies from person to person, in general, the human ear cannot hear outside the 20 Hz to 20 kHz range. In addition, the human ear is more sensitive to certain frequencies, typically between 2 kHz to 4 kHz. The MP3 strategy takes advantage of the naturally masking function of the human ear to mask sound information that a normal human ear can not perceive.

The MP3 strategy implements multiple perceptual codecs to eliminate the sound information inaudible to the human ear. A perceptual codec can be subdivided into multiple discrete tasks. A sound signal can be broken into smaller component pieces called frames, each with a short (fraction of a second) duration. Also, the spectral energy distribution, frequency spread, can be determined by breaking the signal into multiple sub-bands and processing them independently. The frequency spread for each frame can be compared to mathematical models of human psychoacoustics stored in the codec to determine which frequencies need to be rendered accurately. All other frequencies that cannot be perceived by the human ear are removed through masking effects.

While the outer hair cell model and the MP3 strategy provide effective sound processing strategies, neither technique provides a customized contrast enhancement strategy based on the specific needs of an individual CI user. Since no people experience exactly the same hearing loss, there exists a need to provide optimal spectral contrast enhancement tailored to the individual cochlear implant user. The patients who experience a small amount of smearing would perceive spectral contrast enhancement as a distortion of sound, since the smaller spectral peaks would be suppressed. On the other hand, patients who experience a large amount of spectral smearing, would benefit from spectral contrast enhancement. This is because spectral contrast enhancement allows large spectral peaks to be heard, while suppressing the neighboring ones. For patients with a large amount of smearing, neighboring channels introduce noise to the patient, and if suppressed, this noise can be decreased. Therefore to create the optimal amount of spectral enhancement, it is desirable to find out how much spectral smearing is present for the individual patient.

SUMMARY

The methods and apparatus described here implement techniques for clarifying sound as perceived through a cochlear implant. More specifically, the methods and apparatus described here implement techniques for customizing a speech processing strategy in conjunction with psychophysical tests to provide optimal spectral enhancements of contrasts between stimulation signals as perceived through an individual cochlear implant.

In one aspect, a speech processing strategy can be adjusted by determining a spectral modulation transfer function of a cochlear implant user. Once the spectral modulation transfer function is determined, an enhancement filter function can be selected to match the determined spectral modulation transfer function. In addition, filter parameters of the enhancement filter function can be generated based on the spectral modulation transfer function. Then, a speech processing strategy can be adjusted based on the generated filter parameters.

Implementations may include one or more of the following features. For example, a psychophysical test can be administered to the cochlear implant user to determine the spectral modulation transfer function. The psychophysical test administered to the cochlear implant user can include a process of determining a smallest detectable spectral contrast as a function of a plurality of spectral modulation frequency bands. In addition, the enhancement filter function can be selected by comparing the spectral modulation transfer function of the cochlear implant user against a spectral modulation transfer function of a person with normal hearing and determining a ratio of the two spectral modulation transfer functions. The filter parameters can be generated by determining $\sigma$, $G_{max}$, and $G_{min}$, where $\sigma$ represents a width of the filter and $G_{max}$ and $G_{min}$ represents scaling and offset of the filter. Then, a speech processing strategy can be adjusted by adjusting an outer hair cell model based on the filter parameters. The outer hair cell model can be adjusted by determining a plurality of lateral suppression coefficients based on the filter parameters. Further, the filter parameters can be generated by fitting the enhancement filter function to the spectral modulation transfer function.

In another aspect, the techniques include enhancing a spectral contrast for a cochlear implant user by determining a spectral modulation transfer function for a cochlear implant user based on a smallest detectable spectral contrast for a plurality of spectral modulation frequencies. The determined spectral modulation transfer function of the cochlear implant user can be compared to a spectral modulation transfer function of a person having normal hearing. A ratio of the two spectral modulation transfer functions can also be determined to obtain an enhancement factor desired for the cochlear implant user. The techniques can also be implemented to generate filter parameters based on the spectral modulation transfer function and the enhancement factor. Further, the generated filter parameters can be used to adjust a speech processing strategy.

The techniques described in this specification can be implemented to realize one or more of the following advantages. For example, the techniques can be implemented to enhance the contrast between neighboring stimulation signals of a sound processing strategy and thus improve sound clarity and speech recognition, especially under difficult listening conditions. The techniques also can be implemented to provide tailored contrast enhancements for individual CI user. The techniques also can be implemented to decrease the power consumption of a cochlear implant system implementing a sound processing strategy. Further, the techniques can be implemented to reduce interaction between neighboring electrodes and the resulting influence on corresponding neurons by decreasing the stimulation level on one or more electrodes as a result of the stimulation level present on one or more neighboring electrodes.

These general and specific aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION

Figure 1:
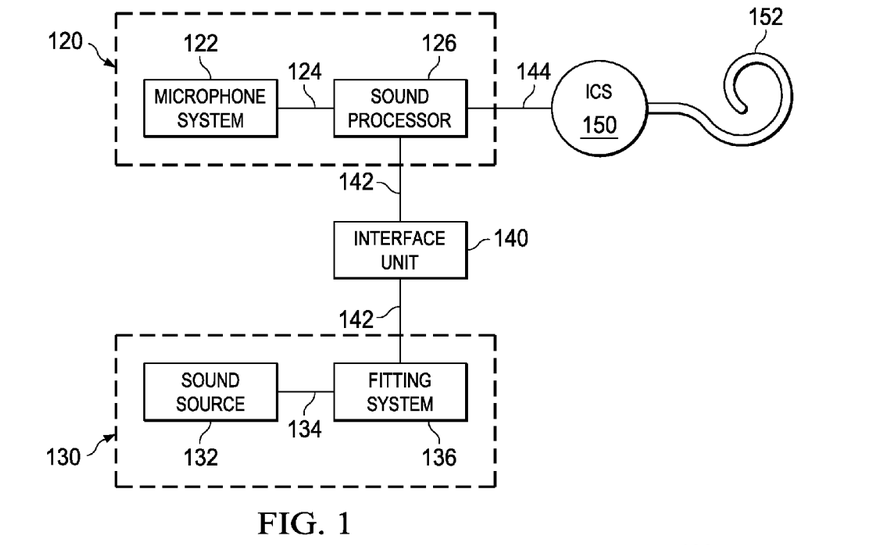
FIG. 1 is a block diagram of a spectral contrast enhancement system.

FIG. 1 represents a spectral contrast enhancement system 100 comprising a cochlear implant fitting portion 130 and a sound processor portion 120. The cochlear implant fitting portion 130 can include a fitting system 136 coupled to a sound source 132 through an appropriate communication link 134. The sound processor portion 120 can include a microphone system 122 coupled to a sound processor 126 through an appropriate communication link 124. The cochlear implant fitting portion 130 can generate an acoustic signal, which can be picked up and processed by the sound processor portion 120. The processed acoustic signal can be passed to an implantable cochlear stimulator (ICS) 150 through an appropriate communication link 144. The ICS 150 is coupled to an electrode array 152 configured to be inserted within the cochlea of a patient. The implantable cochlear stimulator 150 can apply the processed acoustic signal as a plurality of stimulating inputs to a plurality of electrodes distributed along the electrode array 152. The electrode array 152 may be substantially as shown and described in U.S. Pat. Nos. 4,819,647 and 6,129,753, both patents incorporated herein by reference. The sound processor portion 120 may be substantially as shown and described in the co-pending U.S. patent application Ser. No. 11/003,155.

In some implementations, the cochlear implant fitting system 136, the sound source 132, the microphone system 122, and the sound processor 126 can be implemented as an external spectral contrast enhancement portion. The implantable cochlear stimulator 150 and the electrode array 152 can be an internal, or implanted portion. Thus, a communication link 144 coupling the sound processor 126 and the internal portion can be a transcutaneous (through the skin) link that allows power and control signals to be sent from the sound processor 126 to the implantable cochlear stimulator 150.

In other implementations, the implantable cochlear stimulator can send information, such as data and status signals, to the sound processor 126 over the communication link 144. In order to facilitate bidirectional communication between the sound processor 126 and the implantable cochlear stimulator 150, the communication link 144 can include more than one channel. Additionally, interference can be reduced by transmitting information on a first channel using an amplitude-modulated carrier and transmitting information on a second channel using a frequency-modulated carrier.

In an implementation whereby the implantable cochlear stimulator 150 and the electrode array 152 are implanted within the CI user, and the microphone system 122 and the sound processor 126 are carried externally (not implanted) by the CI user, the communication link 144 can be realized through use of an antenna coil in the implantable cochlear stimulator and an external antenna coil coupled to the sound processor 126. The external antenna coil can be positioned to be in alignment with the implantable cochlear stimulator, allowing the coils to be inductively coupled to each other and thereby permitting power and information, e.g., the stimulation signal, to be transmitted from the sound processor 126 to the implantable cochlear stimulator 150. In one implementation, the sound processor 126 and the implantable cochlear stimulator 150 can both be implanted within the CI user, and the communication link 144 can be a direct-wired connection or other suitable link as shown in U.S. Pat. No. 6,308,101, incorporated herein by reference.

The cochlear implant fitting portion 130 of the spectral contrast enhancement system 100 can be implemented to generate a known acoustic signal through the fitting system 136 and to output the acoustic signal through the sound source 132. The microphone system 122 senses the acoustic signal, whereby the acoustic signal can be converted to an electrical signal. The electrical signal can be sent to the sound processor 126 over an appropriate communication link 124, such as a circuit or bus. The sound processor 126 can be implemented to process the electrical signal in accordance with a sound processing strategy selected from various sound processing strategies, and thereby generate a control signal used to control the implantable cochlear stimulator. The control signal can specify or define the polarity, magnitude, location (which electrode pair or group is intended to receive the stimulation current), and timing (when the stimulation current is to be applied to the intended electrode pair or group) of the stimulation signal, such as a stimulation current generated by the implantable cochlear stimulator 150.

In general, magnitude and polarity of the stimulation current applied to the implanted electrodes of the electrode array can be adjusted in accordance with a specified sound processing strategy. The selected sound processing strategy can include defining a pattern of stimulation waveforms that are applied as controlled electrical currents to the electrodes of the electrode array implanted in a patient. Stimulation strategies can be implemented by modulating the amplitude of the stimulation signal or by modulating the frequency of the stimulation signal.

Figure 2:
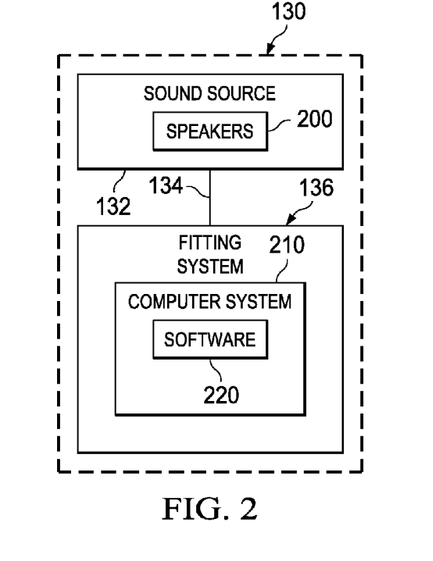
FIG. 2 is a block diagram of a cochlear implant fitting portion.

FIG. 2 represents a functional block diagram of the cochlear implant fitting portion 130. The CI fitting portion 130 facilitates "fitting" of the cochlear implant such that the parameters of the device being fitted are customized for the individual CI user. The CI fitting portion 130 may be substantially as shown and described in U.S. Pat. Nos. 5,626,629 and 6,289,247, both patents incorporated herein by reference. The fitting system 136 of the CI fitting portion 130 can be coupled to a sound source 132 comprising one or more speakers 200 or other suitable sound output devices. The fitting system 136 can further comprise a computer system 210 including a personal computer, portable computer, mobile device, equivalent device, or a combination therein. Referring back to FIG. 1, the fitting system 136 can be coupled to the sound processor 126 through an interface unit (IU) 140, or an equivalent device. A communication link 142 can couple the IU 140 with the sound processor 126. In some implementations, the IU 140 may be included within the computer system 210 of the fitting system 136 as a built-in input/output (I/O) port or implemented as a detachable external device. The computer system 210, with or without the IU 140, can provide input signals to the sound processor 126 that can simulate the acoustic signal sensed by the microphone system 122. Depending on the situation, the input signals generated by the computer system 210 of the fitting system 136 can replace the acoustic signal normally sensed by the microphone system 122 or provide command signals that supplement the acoustical signal sensed through the microphone system 122.

In some implementations, the computer system 210 of the fitting system 136 can include additional peripheral devices including a display device, a storage device, RAM, ROM, input/output (I/O) ports, a keyboard, a mouse, and other suitable peripheral devices. The computer system 120 can be configured to execute software 220 to control reading, displaying, delivering, receiving, assessing, evaluating and/or modifying both acoustic and electric stimulations sent to the sound processor 126. The software 220 can include computer programs such as firmware and other suitable computer executable instructions. The software 220 can facilitate generation of a known acoustic signal, which can be outputted through the sound source 132. The sound source 132 can comprise one or more speakers 200 placed in multiple locations. A display screen can be implemented to display, on a display device, a graphical user interface (GUI) executed as a pat of the software 220 including selection screens, stimulation templates and other information generated by the software 220. The GUI can be implemented to facilitate an audiologist, other medical personnel, or even the CI user to easily view and modify all information necessary to control a fitting process.

In one implementation, the fitting system 136 can be implemented as a stand alone system located at the office of the audiologist or other medical personnel. A stand alone fitting system can allow the audiologist or other medical personnel to customize a sound processing strategy for the CI user during an initial fitting process after the implantation of the CI. The user can return to the office for subsequent adjustments as needed. The return visits may be required because the CI user may not be fully aware of his/her spectral contrast enhancement needs, and the user may become more perceptive of the sound quality provided by the sound processing strategy with the passage of time. The fitting system 136 can be implemented to include simple interfaces using hardware, software, or a combination of both hardware and software. For example, a simple set of hardware buttons, knobs, dials, slides, or similar interfaces can be implemented to select and adjust enhancement parameters. The interfaces can also be implemented as a GUI displayed on a screen.

In one implementation, the fitting system 136 can be implemented as a portable system. A portable fitting system can be implemented to be provided to the CI user as an accessory device for allowing the CI user freedom to adjust the sound processing strategy as needed. The initial fitting process can be performed by the CI user aided by the audiologist or other medical personnel. After the initial fitting process, the user can perform subsequent adjustments without having to visit the audiologist or other medical personnel. The portable fitting system can be implemented to include simple user interfaces using hardware, software, or a combination of both hardware and software to facilitate the adjustment process as described above for the stand alone system implementation.

According to one feature of the techniques for clarifying sound as perceived through a cochlear implant, a fitting process can be implemented to determine a specific spectral contrast modulation strategy for the individual CI user. In one implementation, scaling factors applied to each envelope signals for the outer haircell model, which is described in detail in the co-pending U.S. patent application Ser. No. 11/003,155 and incorporated herein in its entirety by reference, are determined based on spectral modulation threshold function (SMTF) for the individual CI user. The scaling factors thus determined are used to account for the interaction between frequency bands and thereby enhance the contrast between neighboring signals. Since the scaling factors determined are specifically tailored for each individual CI user, the effect of the outer haircell model can be optimized to accurately match the spectral enhancement needs for each individual CI user. Therefore the techniques facilitate implementations of various flexible enhancement systems.

Often times, sensorineural impairments are not limited to auditory sensitivities, and thus requires more than just speech amplification. Listeners with sensorineural hearing loss also suffer from the inability to distinguish individual frequency components of spectrally complex stimuli. Frequency analysis in cochlear processing is analogous to a bank of overlapping band-pass filters, with each of the filters outputting a portion of the total spectrum of sound. In sensorineural impairments, mechanism for analyzing the sound spectrum into channels is altered due to auditory filters that are broader and abnormally asymmetrical. Processing through these abnormal filters may produce smearing of spectral details of the auditory stimuli that renders some portions of spectral contrasts undetectable. This is due to a reduction in the perceivable amplitude between peaks and valleys, which renders identification of specific frequency regions of energy concentration difficult to identify. Since frequency locations of spectral peaks are crucial cues to identity of speech sounds, spectral flattening may result in decreased speech perception ability.

In some implementations, to determine the scaling factors specific for each individual CI user, a psychophysical test is administered to the CI user using the CI fitting portion 136 whereby the smallest detectable spectral contrast can be determined for each spectral modulation frequency. For a given CI user, the SMTF describes the ability of the CI user to discriminate between a complex stimulus with an unmodulated or flat spectrum such as a white noise and one that has a sinusoidal ripple imposed on its spectrum. Each stimulus is composed of multiple tonal components spaced logarithmically across a frequency axis to ensure equal numbers of tonal components defined in each ripple cycle across the stimulus bandwidth. Stimuli are generated with random starting phase values for each tonal component. The flat spectrum stimulus is generated with all tonal components having equal amplitude, and the ripple-spectrum stimuli contains variations in component amplitudes that are sinusoidal in log-log units, with ripple periods distributed over the logarithm of frequency, and the ripple amplitude described in decibels. Frequency of ripple determined the spacing of peaks and valleys across the frequency range, and the amplitude of the ripple corresponds to the amount of spectral contrast present in the stimulus. Ripple frequencies are arranged in cycles per octave (CPO) and the ripple amplitude is varied during the test.

A CI user is seated in a sound-treated booth with a touchscreen for recording his responses to stimuli heard through a headphone. For each ripple frequency, the ripple amplitude is incrementally increased or decreased until a set percentage of correct discrimination is achieved. For each presentation to the CI user, multiple combination of stimuli are presented consecutively including one rippled spectrum of selected ripple frequency and one or more flat spectrum stimuli. When one flat spectrum stimulus and one rippled stimulus is presented, the CI user is asked to determine if the two stimuli are different. When two flat spectrum stimuli and one rippled stimulus are presented consecutively, the CI user is asked to select which stimulus is different from the other two stimuli. The ripple amplitude is initiated at a set dB (for example, 20 dB) peak-to-valley and increased by a small dB level (for example, 2 dB) after each incorrect response and decreased by a small dB level after each correct response. The dB step size is decreased (for example, to 0.5 dB) after a set number of reversals of directions (for example, four reversals) and the ripple amplitudes after a set number of reversals (for example ten reversals) are averaged. The average ripple amplitude represents the point at which the CI user is able to distinguish the rippled stimulus from the flat stimuli. This corresponds to a threshold value of the amplitude of modulation needed at a particular CPO. If the rippled stimulus is made very fast by increasing the number of cycles/octave, the CI user will need more spectral contrast to differentiate between the flat spectrum stimuli and the rippled stimuli. In general, the SMTF will show characteristics of lower modulation detection threshold at lower cpo and higher threshold at higher cpo. Therefore, the spectral contrast may need to be increased more at higher cpo than at lower cpo.

Figure 3:
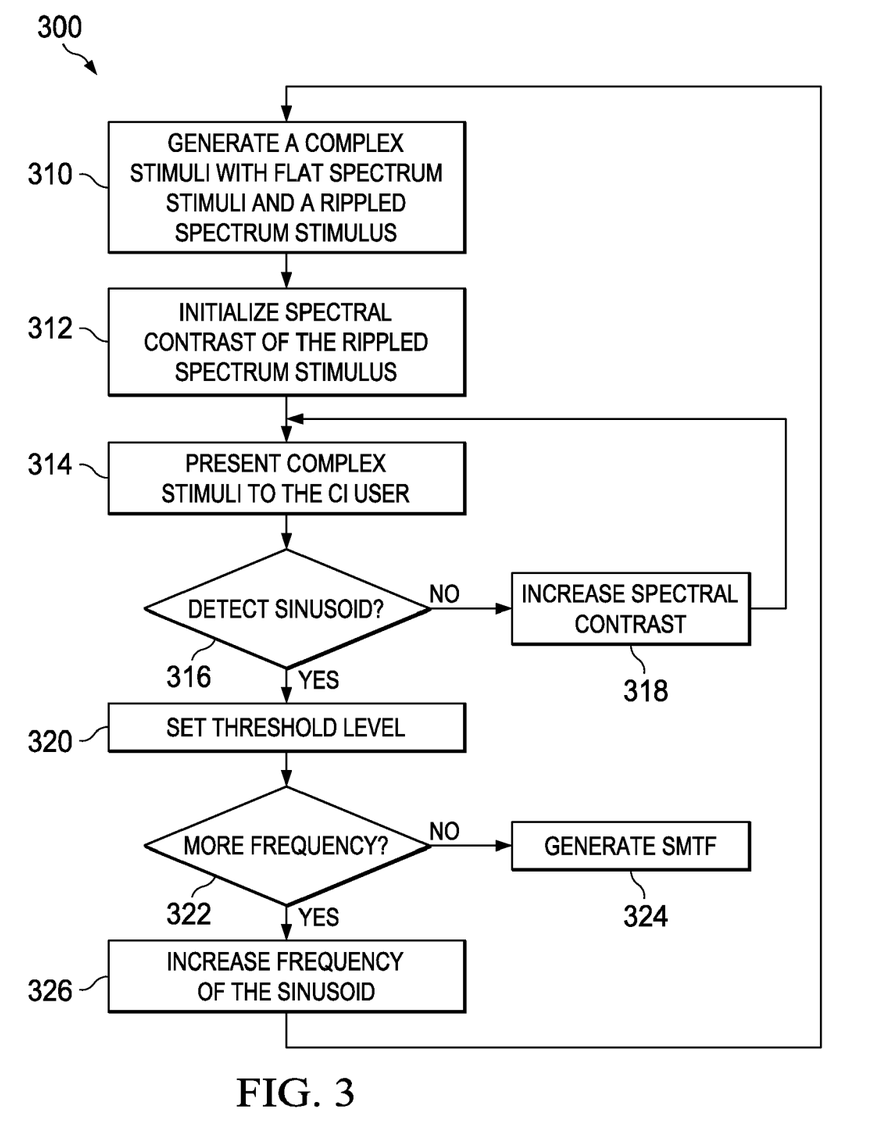
FIG. 3 is a flow chart describing a process of administering a SMTF psychophysical test to an individual cochlear implant user.

FIG. 3 describes a process of performing the psychophysical test 300 to determine the SMTF of the CI user. At 310, a complex stimulus including a flat spectrum stimulus and a rippled-spectrum stimulus is generated across a logarithmic frequency axis. The rippled spectrum stimulus is sinusoidal and can have a starting phase randomly selected from a range of 0 to $2\pi$. The rippled spectrum stimulus may be initialized, at 312, to a ripple amplitude corresponding to a spectral contrast too small for the CI user to distinguish the rippled spectrum stimulus from the flat spectrum stimuli. At 314, the sinusoidal rippled spectrum stimulus and one or more flat spectrum stimuli can be delivered to the CI user for detection. If the CI user is able to detect the difference between the sinusoidal rippled spectrum stimulus and the flat spectrum stimulus at 316, the amplitude level of the sinusoidal stimulus corresponding to the spectral contrast applied is noted as the threshold level for the frequency space (in cpo) at 320. If the CI user is not able to detect the sinusoidal rippled spectrum stimulus, the spectral contrast can be increased in small increments at 318 until a threshold level is reached, whereby the CI user is able to discriminate the sinusoidal rippled spectrum stimulus from flat spectrum stimuli. At 322, a determination is made if any more thresholds need to be obtained for other spectral modulation frequencies. If threshold values have been determined at all the necessary spectral modulation frequencies, the SMTF is generated at 324 as a function of cpo. If threshold needs to be measured for additional spectral modulation frequencies, the number of cycles in the sinusoidal rippled spectrum stimulus are either increased or decreased as needed at 326. New complex stimuli are generated at 310, and 312 through 324 are repeated until a threshold level is determined for each available frequency band. The number of available frequency bands may correspond to the total number of electrodes implemented in the electrode array 152 of the internal or implanted portion.

Figure 4:
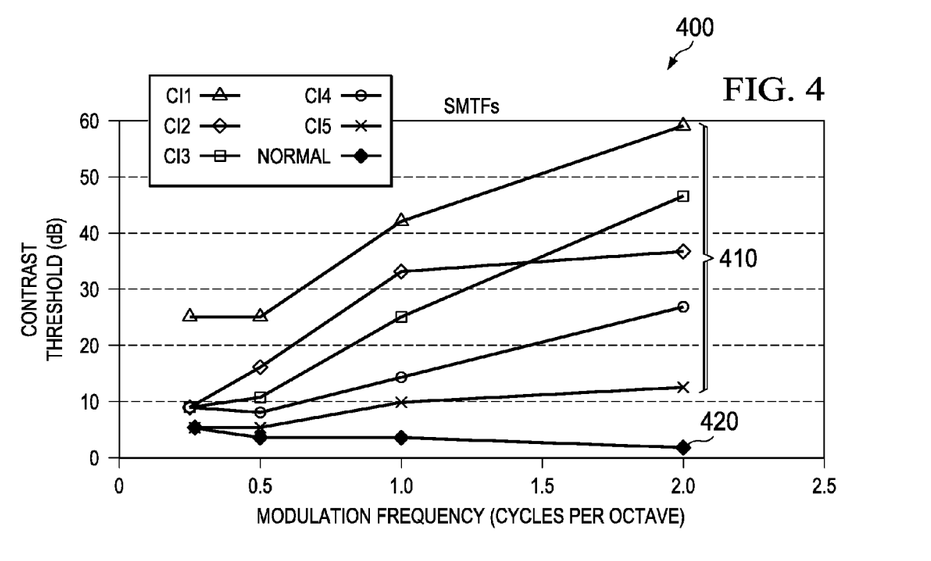
FIG. 4 represents a graph of SMTFs of cochlear implant users listening without any spectral contrast enhancement strategy.

FIG. 4 depicts a sample SMTF chart 400 illustrating SMTFs determined for multiple CI users listening through a non-enhanced sound processing strategy 410. In addition, the average SMTF for listeners with normal hearing 420 is also represented. The ratio between the SMTF of the CI user and a normal hearing listener provides the optimal amount of spectral enhancement for the CI user. Then, a sound processing strategy may be adjusted to provide the optimal spectral contrast enhancement for different modulation frequencies specifically tailored to the CI user.

Figure 5:
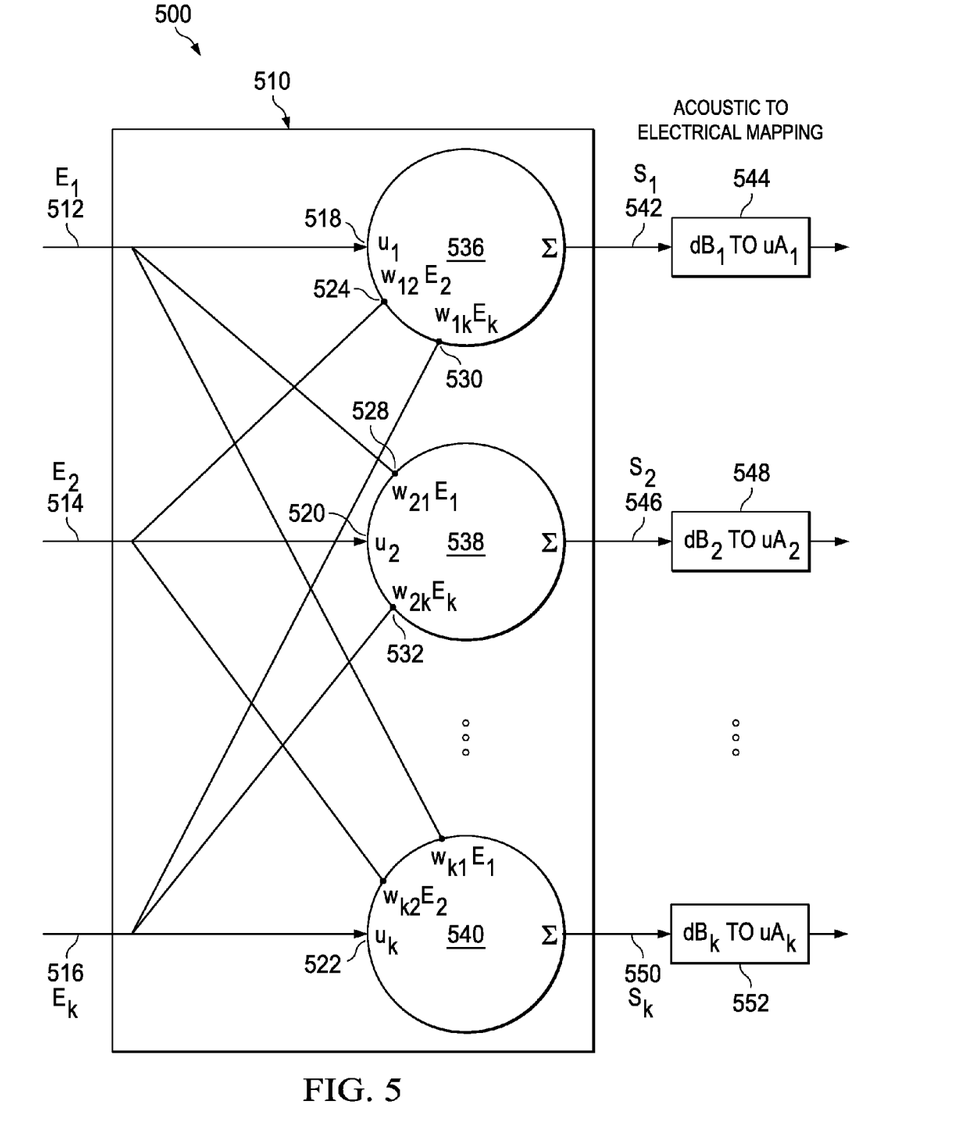
FIG. 5 is a functional block diagram of a lateral suppression network of a sound processing system.

FIG. 5 represents a functional diagram detailing an implementation of a lateral suppression network 510 as it relates to the system 500 of the outer hair cell model as described in the co-pending U.S. patent application Ser. No. 11/003,155. Lateral suppression is the term used to describe the psychophysical effect by which the loudness perceived from one tone is diminished to some extent by the presence of a neighboring tone. The suppressive effect is particularly evident when a loud tone closely neighbors a quieter tone. Thus, lateral suppression operates to enhance the contrast between tones. However, the lateral suppression algorithm must be implemented such that it does not generate abnormal results. If a flat spectrum is input to the lateral suppression network 510, a flat spectrum should also be output from the lateral suppression network 510. Further, the lateral suppression network must account for the frequency bands representing the highest and lowest frequencies of the audio signal (now shown), the edge frequency bands. In the system 500, for example, the first frequency band and the $k_{th}$ frequency band are the edge frequency bands. Because only one frequency band is immediately adjacent to each edge frequency band, each edge frequency band would be subjected to less suppression without additional compensation. Therefore, the lateral suppression network 510 must compensate by adjusting one or more factors, such as the weighting factor u associated with the edge frequency band or one or more of the scaling factors w employed by the lateral suppression processor associated with the edge frequency band.

The suppressed signals output from the lateral suppression network 510 are converted to electrical signals using the acoustic-to-electrical mapping associated with the corresponding frequency bands and provided as stimulation signals to one or more electrode pairs of a cochlear implant. For example, the envelope signals $E_1$ 512, $E_2$ 514, and $E_k$ 516 output from the bank of envelope detectors (not shown) are input into the lateral suppression network 510. The lateral suppression network 1010 then suppresses one or more of the envelope signals $E_1$ 512, $E_2$ 514, and $E_k$ 516 in accordance with envelope signals associated with neighboring frequency bands, including the envelope signals $E_1$ 512, $E_2$ 514, and $E_k$ 516. The lateral suppression network 510 then outputs the corresponding suppressed signals $S_1$ 542, $S_2$ 546, and $S_k$ 550 respectively.

The suppressed signal $S_1$ 542 associated with the first frequency band is then converted into an electrical signal using the acoustic-to-electrical mapping 544 corresponding to the first frequency band. Similarly, the suppressed signal $S_2$ 546 associated with the second frequency band is then converted into an electrical signal using the acoustic-to-electrical mapping 548 corresponding to the second frequency band. Additionally, the suppressed signal $S_k$ 550 associated with the $k_{th}$ frequency band is then converted into an electrical signal using the acoustic-to-electrical mapping 552 corresponding to the $k_{th}$ frequency band.

In one implementation, the envelope signals $E_1$ 512, $E_2$ 514, and $E_k$ 516 are provided as inputs to the lateral suppression network 500. In the lateral suppression network 500, each envelope signal can be combined with one or more scaled envelope signals to account for the influence that envelope signals associated with neighboring frequency bands have on a particular envelope signal.

One or more of the envelope signals output from the bank of envelope detectors (not shown) can be weighted by a factor $u_i$ upon being provided to the lateral suppression network 510, where i represents the frequency band with which the envelope signal is associated. Thus, an envelope signal that is determined to be of greater importance than the envelope signals associated with neighboring frequency bands can be emphasized, such as an envelope signal representing an amplitude that exceeds a particular threshold value. Further, an envelope signal determined to be of lesser importance can be deemphasized, such as an envelope signal representing an amplitude that falls below a particular threshold value. In an implementation, each of the envelope signals provided to the lateral suppression network 510 can be weighted, and the weight associated with envelope signals that should not be emphasized or deemphasized can be set to 1.

For example, the envelope signals $E_1$ 512, $E_2$ 514, and $E_k$ 516 output from the bank of envelope detectors (not shown) are provided as inputs to the lateral suppression network 510. The lateral suppression processor 516 corresponding to the first frequency band multiplies the envelope signal $E_1$ 512 by a weighting factor $u_1$ 518 associated with the first frequency band. Similarly, the lateral suppression processor 538 corresponding to the second frequency band multiplies the envelope signal $E_2$ 514 by a weighting factor $u_2$ 520 associated with the second frequency band. The lateral suppression processor 540 corresponding to the $k_{th}$ frequency band multiplies the envelope signal $E_k$ 516 by a weighting factor $u_k$ 522 associated with the $k_{th}$ frequency band. As a result, the suppressive effect of signals associated with neighboring frequency bands will be diminished on envelope signals deemed to be of greater importance and increased on envelope signals deemed to be of lesser importance.

Because the influence that an envelope signal has on a neighboring envelope signal decreases as the number of frequency bands separating the envelope signals increases, the scaling factor applied to an envelope signal to generate a scaled envelope signal is selected as a function of the separation between the neighboring frequency bands. Therefore, a scaling factor $w_{ij}$ is chosen, where i represents the frequency band associated with the envelope signal being suppressed and j represents the frequency band associated with the envelope signal that is producing the suppressive effect. With each increase in the frequency band separation, the scaling factor $w_{ij}$ will further decrease the magnitude of the envelope signal being scaled. Additionally, as scaled envelope signals suppress an envelope signal, the scaling factor represents a negative value.

A laterally suppressed signal $S_i$ is generated by combining an envelope signal associated with a particular frequency band $E_i$ with one or more scaled envelope signals $w_{ij}E_j$ associated with neighboring frequency bands. As discussed above, the envelope signal being suppressed also can be weighted using a weighting factor $u_i$. The combining operation can be expressed mathematically as shown in Equation 1.

$$S_i = u_i E_i + \sum_{j \neq i} w_{ij} E_j \tag{1}$$

Because nonlinearities are known to exist in the response of the basilar membrane, Equation 1 can be generalized as expressed in Equation 2, where $F_i(x)=X$ and $w_{ij}=0$. However, this simplification is not required and $S_i$ can be generated using a non-linear function in another implementation.

$$S_i = u_i E_i + F_i\left(\sum_j w_{ij} E_j\right) \tag{2}$$

In an implementation, the envelope signal $E_1$ 512 associated with the first frequency band is provided to a corresponding lateral suppression processor (not shown). The lateral suppression processor 536 then multiplies the envelope signal $E_1$ 512 by the weighting factor $u_1$ 518. The lateral suppression processor 536 also receives as input the scaled envelope signal $w_{12}E_2$ 524, which represents the interaction of the envelope signal $E_2$ 514 associated with the second frequency band with the envelope signal $E_1$ 512 associated with the first frequency band. Additionally, the lateral suppression processor 536 receives as input the scaled envelope signal $w_{1k}E_k$ 530, which represents the interaction of the envelope signal $E_k$ 516 associated with the $k_{th}$ frequency band with the envelope signal $E_1$ 512 associated with the first frequency band. Further, the lateral suppression processor 536 can also receive as inputs the scaled envelope signals associated with any or all of the remaining third through K−1$_{th}$ frequency bands.

The lateral suppression processor 536 combines the envelope signal $E_1$ 512, weighted by $u_1$ 518, with at least the scaled envelope signals $w_{12}E_2$ 524 and $w_{1k}E_k$ 530, and outputs a laterally suppressed signal $S_1$ 542 associated with the first frequency band. The laterally suppressed signal $S_1$ 542 can then be converted to an electrical stimulation signal using the acoustic-to-electrical mapping 544 corresponding to the first frequency band.

A similar lateral suppression operation can be carried out for any or all of the envelope signals associated with the remaining frequency bands. For example, the lateral suppression processor 538 receives the envelope signal $E_2$ 514 associated with the second frequency band. The lateral suppression processor 538 then multiplies the envelope signal $E_2$ 514 by the weighting factor $u_2$ 520. The lateral suppression processor 538 also receives as inputs the scaled envelope signals $w_{21}E_1$ 528 and $w_{2k}E_k$ 532, which are associated with the first and $k_{th}$ frequency bands respectively. Additionally, the lateral suppression processor 538 can receive as inputs the scaled envelope signals associated with any or all of the remaining frequency bands. The lateral suppression processor 538 combines the envelope signal $E_2$ 514, weighted by $u_2$ 520, with the scaled envelope signals $w_{21}E_1$ 528 and $w_{2k}E_k$ 532, and outputs a laterally suppressed signal $S_2$ 546 associated with the second frequency band. The laterally suppressed signal $S_2$ 546 is then converted to an electrical stimulation signal using the acoustic-to-electrical mapping 548 associated with the second frequency band.

In an implementation, each lateral suppression processor of the lateral suppression network 510 can be configured to receive as inputs the scaled envelope signals associated with each of the neighboring frequency bands. Therefore, each of the envelope signals can be suppressed by scaled envelope signals associated with each of the neighboring frequency bands. If an envelope signal $E_b$ should not be used to suppress an envelope signal $E_a$, the scaling factor $w_{ab}$ can be set to 0.

Figure 6:
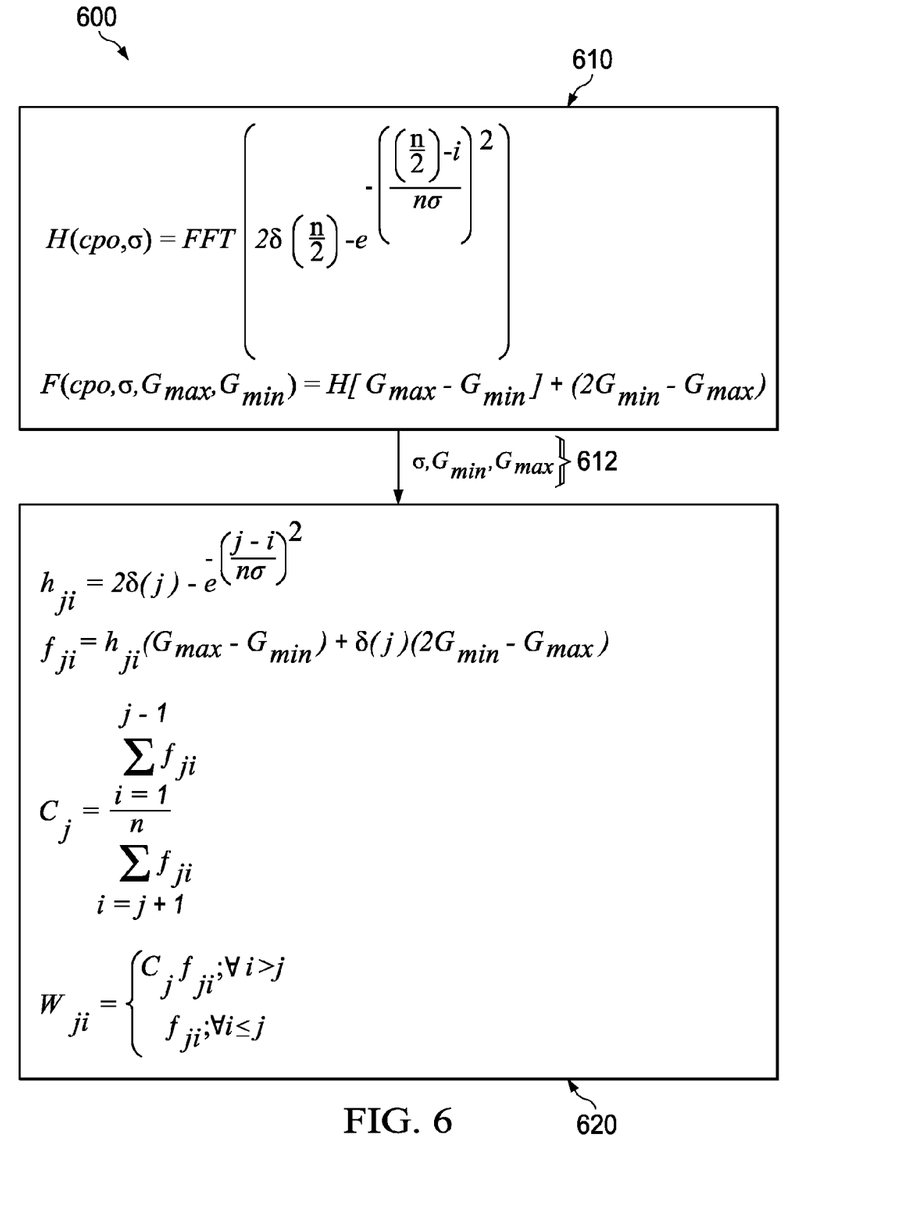
FIG. 6 describes a list of mathematical operations used to adjust a sound processing strategy based on the determined SMTF of the individual cochlear implant user.

FIG. 6 is a block diagram describing a process of adjusting a sound processing strategy 600 based on the outer haircell model as described in the co-pending U.S. patent application Ser. No. 11/003,155, which involves adjusting the "lateral suppression" coefficients. The adjustment process may be described in two steps. At 610, the SMTF determined for the CI user is analyzed to generate filter parameters 612 that best describe the SMTF. At 620, the filter parameters are applied in determining scaling factors for enhancement filters of the outer haircell model. Equations (1) and (2) describe functions used to determine the parameters based on SMTF of the CI user, and Equations (3), (4), (5), and (6) describe functions used to apply the filter parameters to determine the scaling factors of the enhancement filters in the outer haircell model. The equations are described more in detail below.

$$H(cpo, \sigma) = FFT\left(2\delta\left(\frac{n}{2}\right) - e^{-\left(\frac{\left(\frac{n}{2}\right)-i}{n\sigma}\right)^2}\right) \tag{3}$$

$$F(cpo, \sigma, G_{max}, G_{min}) = H[G_{max} - G_{min}] + (2G_{min} - G_{max}) \tag{4}$$

$$h_{ji} = 2\delta(j) - e^{-\left(\frac{j-i}{n\sigma}\right)^2} \tag{5}$$

$$f_{ji} = h_{ji}(G_{max} - G_{min}) + \delta(j)(2G_{min} - G_{max}) \tag{6}$$

$$C_j = \frac{\sum_{i=1}^{j-1} f_{ji}}{\sum_{i=j+1}^{n} f_{ji}} \tag{7}$$

$$W_{ji} = \begin{cases} C_j f_{ji}; \forall\, i > j \\ f_{ji}; \forall\, i \leq j \end{cases} \tag{8}$$

Figure 7:
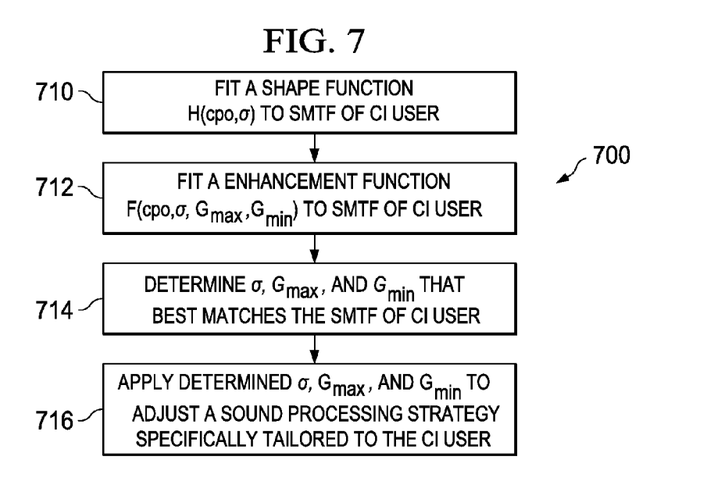
FIG. 7 is a flow chart describing a process of determining filter parameters based on the SMTF of the individual cochlear implant user.
Figure 8A:
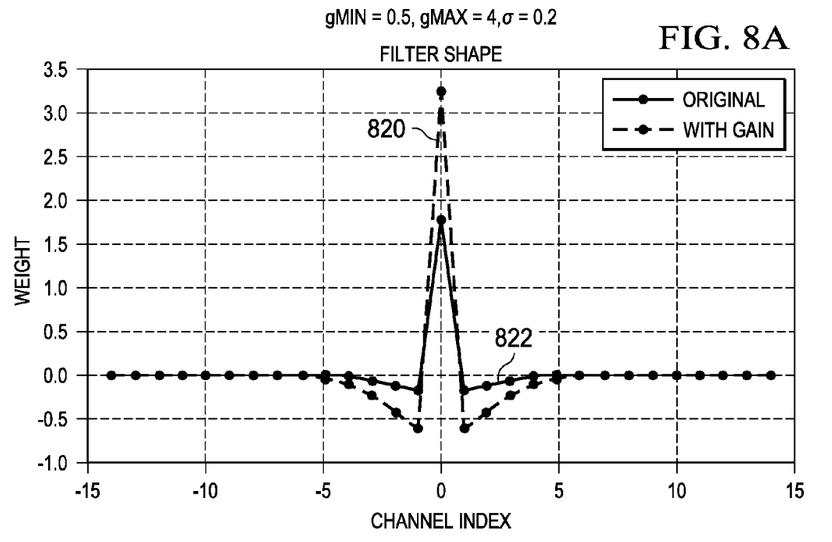
FIG. 8A is a graph illustrating the effect of filter parameters on the enhancement filter and scaling factor (weight).
Figure 8B:
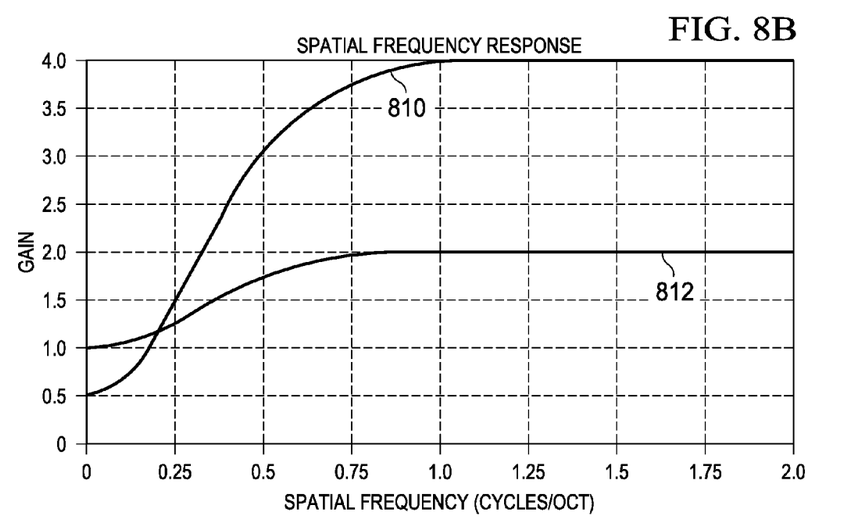
FIG. 8B is a graph illustrating the improvement in fitting a function to the SMTF by using $G_{max}$ and $G_{min}$ in comparison to a function using $\sigma$ alone.
Figure 9:
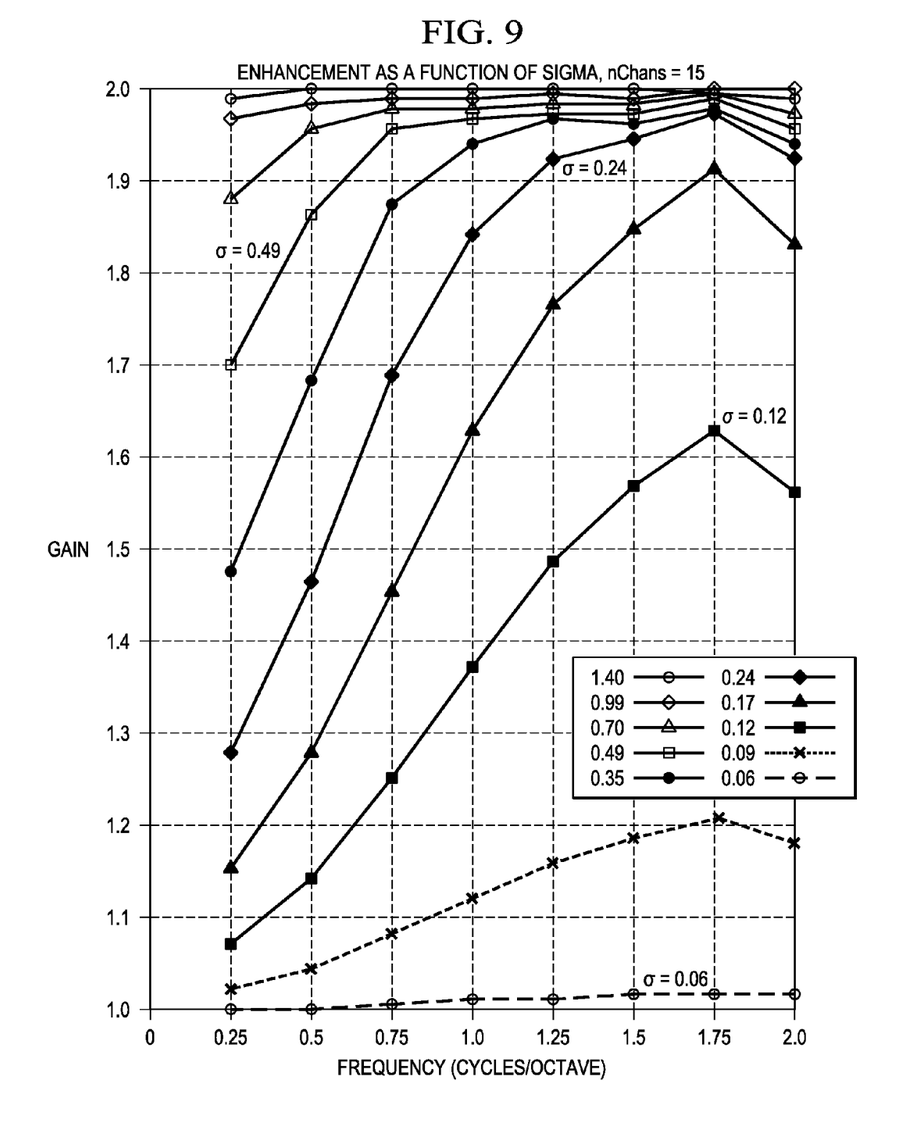
FIG. 9 is a graph listing various enhancement profiles plotted as a function of cpo by varying the value of $\sigma$.

FIG. 7 describes a process of determining the filter parameters corresponding to 610 above. A mathematical representation of threshold levels as a function of the available frequency band can be generated to define a spectral modulation transfer function (SMTF) of the CI user. The SMTF for the CI user is analyzed to generate at least three filter parameters, $\sigma$, $G_{max}$, and $G_{min}$. These filter parameters are generated by fitting a function to the SMTF of the CI user. At 710, a shape function H (cpo, $\sigma$) is generated and fit to the curve of the SMTF of the CI user to find the ideal $\sigma$ that best describes the shape of the curve. The shape function (1), H (cpo, $\sigma$), is a Fast Fourier Transform (FFT) of a generalized function for a central filter, $h_{ji}$. At 712, the shape function is modified to incorporate scaling and offset to generate an enhancement function (2), F (cpo, $\sigma$, $G_{max}$, $G_{min}$), which is fit to the SMTF of the CI user to find the ideal $G_{max}$ and $G_{min}$ values to add scaling and offset in addition to the shape provided by σ. By incorporating the contribution of $G_{max}$ and $G_{min}$, the SMTF can be matched even better than possible with just σ. FIG. 8B depicts the improvement in the fit provided by the enhancement function (2), F (cpo, σ, $G_{max}$, $G_{min}$) 810 compared to the shape function (1), H (cpo, σ) 812. At 714, σ, $G_{max}$, and $G_{min}$ are determined from the enhancement function. In addition, FIG. 9 illustrates a list of possible F (cpo, σ, $G_{max}$, $G_{min}$) that were fit to the SMTF of the CI user as a function of frequency. Each curve profile represents the effect of applying different σ values to the function. Typically, the profile that best fits the optimal enhancement requirement of the individual CI user may be selected to determine the ideal σ. Appropriate sound processing strategy can be adjusted based on the determined σ, $G_{max}$, and $G_{min}$ to provide customized spectral enhancement strategy for the individual CI user at 716.

Figure 10:
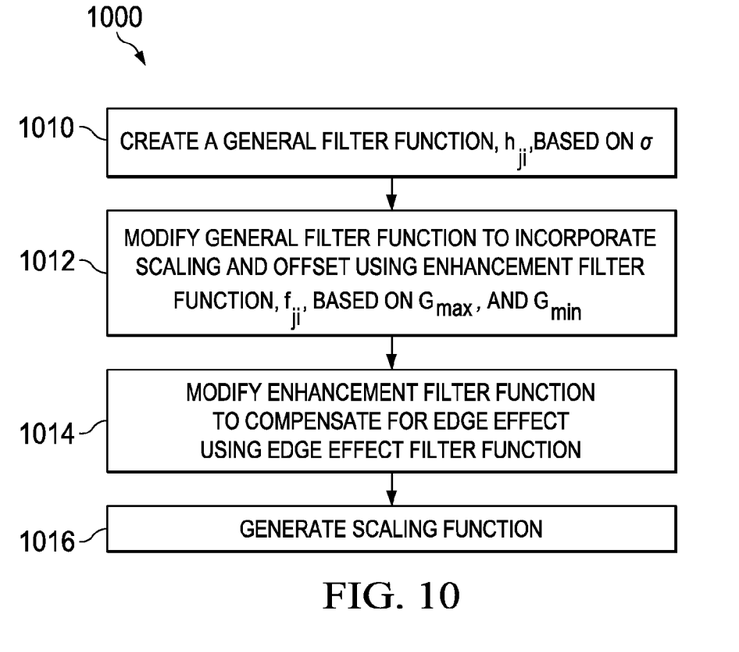
FIG. 10 is a flow chart describing a process of generating scaling factors based on the filter parameters $\sigma$, $G_{max}$, and $G_{min}$.

The filter parameters, σ, $G_{max}$, and $G_{min}$, can be used to determine the scaling factors, or the lateral suppression coefficients of the outer hair cell model customized for the individual CI user at 620 of FIG. 6 above. FIG. 10 depicts a process of determining the scaling factors applied to the outer haircell model. At 1010, a general filter function, $h_{ji}$ (3) is generated based on the σ determined for the CI user. Variable "j" represents the filter for which the enhancement is being calculated; variable "i" represents filter number; and constant "n" represents the number of channels corresponding to the number of electrodes implemented in the internal or implanted portion of the cochlear implant. A plot of function $h_{ji}$ 820 with respect to filter number, "i", is illustrated in FIG. 8A. The scaling factor for filter "j" is positive and the contributions from all other filters are subtracted to arrive at the gain enhancement shown. At 1012, the general filter function (3), $h_{ji}$, is modified by taking into account the contributions of $G_{max}$ and $G_{min}$, which scales and offsets the general filter function (3), $h_{ji}$. This scaling and offset modification is implemented using an enhancement filter function (4), $f_{ji}$. A plot of function $f_{ji}$ 822 with respect to filter number, "i", is illustrated in FIG. 8A. At 1014, the enhancement filter function (4), $f_{ji}$ is modified to take into account the edge effect. This edge effect modification is implemented using an edge effect filter function (5), $c_{ji}$. Since a finite number of filters are implemented on left and right sides of the filter, "j", there may be imbalance between the two sides. To compensate for the imbalance, an integral of the right side and the left side is calculated and if one side is larger than the other side, the smaller side is made bigger. At 1016, the contributions of the general filter function (3), $h_{ji}$, the enhancement filter function (4), $f_{ji}$ and edge effect filter function (5), $c_{ji}$, are combined to generate the scaling function (6), $W_{ji}$, which represents the scaling factor for each filter i, given filter j for which the enhancement is being calculated. The output of this scaling factor is the sum of the value for filter j added with the values of all other filters. The scaling factor generated for each filter is used to adjust the "lateral suppression" coefficients of the outer hair cell model.

In some implementations, the techniques may be used to adjust an MP3 sound processing strategy. Two masking effects are implemented in the MP3 strategy to eliminate sounds that cannot be perceived by the human ear. A simultaneous masking effect or "auditory masking" is dependent on the relationship between frequencies and their relative loudness. If a sound is close in frequency to a second sound, it is difficult for the human ear to distinguish the two sounds. Thus the simultaneous masking effect masks the sound with less information (lower frequency). In addition to simultaneous masking is dependent on time delay between two sounds. If a loud sound and a quiet sound are played simultaneously, the human ear cannot hear the quiet sound. However, if the same two sounds are played with a significant time delay in-between, the human hear is able to hear both sounds.

Thus, temporal masking determines the length of time between the two sounds at which the second sound becomes audible. The length of time is set as a threshold for masking the quieter sound.

Figure 11:
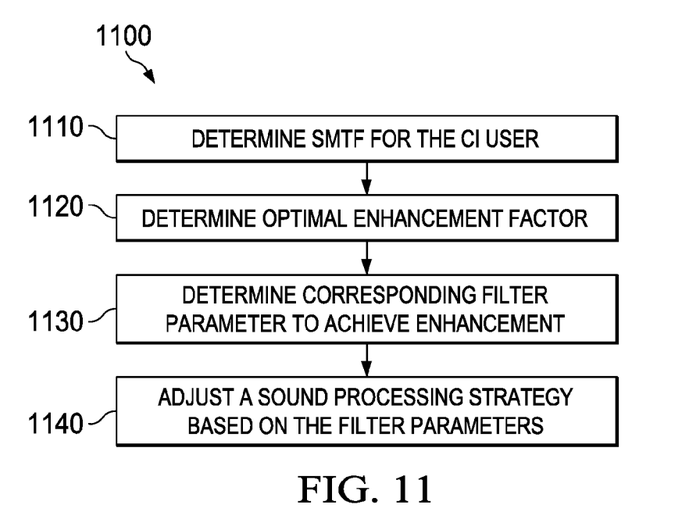
FIG. 11 is a flow chart of a spectral contrast enhancing process.

FIG. 11 describes a general process of optimizing a spectral contrast enhancement strategy 1100 customized for the individual CI user. At 1110, a spectral modulation transfer function of a cochlear implant user is determined. At 1120, an enhancement factor for the determined spectral modulation transfer function is determined. At 1130, filter parameters are generated based on the spectral modulation transfer function and the enhancement factor. At 1140, a speech processing strategy is adjusted based on the generated filter parameters.

In some implementations, the techniques for adjusting a contrast enhancement strategy as described in FIGS. 1-11 may be implemented using one or more computer programs comprising computer executable code stored on a computer readable medium and executing on the computer system 210, the sound processor portion 120, or the CI fitting portion 130, or all three. The computer readable medium may include a hard disk drive, a flash memory device, a random access memory device such as DRAM and SDRAM, removable storage medium such as CD-ROM and DVD-ROM, a tape, a floppy disk, a CompactFlash memory card, a secure digital (SD) memory card, or some other storage device. In some implementations, the computer executable code may include multiple portions or modules, with each portion designed to perform a specific function described in connection with FIGS. 3, 6, 7, 10, and 11 above. In some implementations, the techniques may be implemented using hardware such as a microprocessor, a microcontroller, an embedded microcontroller with internal memory, or an erasable programmable read only memory (EPROM) encoding computer executable instructions for performing the techniques described in connection with FIGS. 3, 6, 7, 10, and 11. In other implementations, the techniques may be implemented using a combination of software and hardware.

Processors suitable for the execution of a computer program include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of implementations have been disclosed herein. Nevertheless, it will be understood that various modifications may be made without departing from the spirit and scope of the claims. Accordingly, other implementations are within the scope of the following claims.

What is claimed is:

1. A method for enhancing a cochlear implant's spectral contrast using a computerized fitting system, the method comprising:
   providing from the fitting system acoustic signals with different frequency spectrums to a cochlear implant implanted in a user;
   receiving at the fitting system user responses to the acoustic signals, wherein the responses indicate the user's ability to discriminate between frequencies in a spectrum;
   determining in the fitting system a transfer function of the cochlear implant based upon the user's responses; and
   configuring the cochlear implant, based on the transfer function, to modify at least one contrast between frequencies processed by a processor in the cochlear implant.

2. The method of claim 1, wherein providing the acoustic signals comprises:
   applying to the cochlear implant a flat spectrum signal comprising spectral components of equal amplitude;
   applying to the cochlear implant a ripple spectrum signal comprising spectral components that vary in amplitude as a function of frequency; and
   wherein the user responses indicate a smallest amplitude variation of the ripple spectrum signal detectable by the user when compared to the flat spectrum.

3. The method of claim 2, wherein the ripple spectrum has a ripple period.

4. The method of claim 3, wherein the ripple period is measured in cycles per octave.

5. The method of claim 3, further comprising repeating the steps of claim 2 at a plurality of different ripple periods.

6. The method of claim 2, wherein the smallest amplitude variation is determined for each of a plurality of ripple periods measured in cycles per octave.

7. The method of claim 2, wherein the smallest amplitude variation detectable by the user comprises the amplitude at which the user correctly differentiates a ripple spectrum signal from the flat spectrum signal at least a predetermined percentage of the time.

8. The method of claim 2, wherein the flat spectrum signal and the ripple spectrum signal are each presented to the user consecutively.

9. The method of claim 1, wherein configuring the cochlear implant is further based on a ratio of the transfer function and a transfer function of a person with normal hearing.

10. A method for enhancing a cochlear implant's spectral contrast using a computerized fitting system, the method comprising:
    providing from the fitting system acoustic signals with different frequency spectrums to a cochlear implant implanted in a user;
    receiving at the fitting system user responses to the acoustic signals, wherein the responses indicate the user's ability to discriminate between frequencies in a spectrum;
    determining in the fitting system a transfer function of the cochlear implant based upon the user's responses; and
    configuring the cochlear implant, based on the transfer function, to modify scaling factors used by a processor in the cochlear implant, wherein the scaling factors adjust at least one contrast between different frequencies processed by the processor.

11. The method of claim 10, wherein providing the acoustic signals comprises:
    applying to the cochlear implant a flat spectrum signal comprising spectral components of equal amplitude;
    applying to the cochlear implant a ripple spectrum signal comprising spectral components that vary in amplitude as a function of frequency; and
    wherein the user responses indicate a smallest amplitude variation of the ripple spectrum signal detectable by the user when compared to the flat spectrum.

12. The method of claim 11, wherein the ripple spectrum has a ripple period.

13. The method of claim 12, wherein the ripple period is measured in cycles per octave.

14. The method of claim 12, further comprising repeating the steps of claim 11 at a plurality of different ripple periods.

15. The method of claim 11, wherein the smallest amplitude variation is determined for each of a plurality of ripple periods measured in cycles per octave of spectrum frequency.

16. The method of claim 11, wherein for a given ripple period the smallest amplitude variation detectable by the user comprises the amplitude at which the user correctly differentiates a ripple spectrum signal from the one or more flat spectrum signals at least a predetermined percentage of the time.

17. The method of claim 11, wherein the flat spectrum signal and the ripple spectrum signal are each presented to the user consecutively.

18. The method of claim 10, wherein configuring the cochlear implant is further based on a ratio of the transfer function and a transfer function of a person with normal hearing.

19. The method of claim 10, wherein the scaling factors account for the interaction between frequency bands and thereby enhance the contrast between neighboring signals.

20. A method for enhancing a cochlear implant's spectral contrast, the method comprising:
    receiving an audio signal at the cochlear implant implanted in a user;
    filtering the audio signal into a plurality of envelope signals, wherein each envelope signal is associated with a frequency band within the audio signal; and
    generating suppressed signals by processing the envelope signals using one or more scaling factors that are based on a transfer function indicative of the user's ability to discriminate between frequencies in a spectrum, wherein the transfer function results from feedback from the user in response to known acoustic signals.

21. The method of claim 20, wherein generating each of the suppressed signals comprises combining a first envelope signal $E_i$ and one or more envelope signals $E_j$ other than the first envelope signal, and wherein the first envelope signal is adjusted by a weighting factor $u_i$ and the one or more envelope signals are each adjusted by at least one of the one or more scaling factors $w_{ij}$.

22. The method of claim 21, wherein each of the suppressed signals is expressed by the equation $$S_i = u_i E_i + \sum_{j \neq i} w_{ij} E_j.$$

* * * * *